(12) United States Patent
Eidenschink et al.

(10) Patent No.: US 7,951,186 B2
(45) Date of Patent: May 31, 2011

(54) EMBEDDED ELECTROACTIVE POLYMER STRUCTURES FOR USE IN MEDICAL DEVICES

(75) Inventors: Tracee Eidenschink, Wayzata, MN (US); Jan Weber, Maastricht (NL); Karl A. Jagger, Deephaven, MN (US); Matt Heidner, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 282 days.

(21) Appl. No.: 11/411,277

(22) Filed: Apr. 25, 2006

(65) Prior Publication Data
US 2007/0247033 A1 Oct. 25, 2007

(51) Int. Cl.
*A61F 2/06* (2006.01)

(52) U.S. Cl. .................................................. 623/1.11

(58) Field of Classification Search .................. 606/192, 606/194; 604/264; 623/1.11; 310/800
See application file for complete search history.

(56) References Cited

U.S. PATENT DOCUMENTS

| | | | |
|---|---|---|---|
| 4,490,421 A | 12/1984 | Levy | 428/35 |
| 4,874,735 A | 10/1989 | O'Brien et al. | 502/159 |
| 4,933,052 A | 6/1990 | O'Brien et al. | 204/58.5 |
| 5,147,302 A * | 9/1992 | Euteneuer et al. | 604/103 |
| 5,449,722 A | 9/1995 | Nishida et al. | 525/98 |
| 5,573,520 A | 11/1996 | Schwartz et al. | 604/282 |
| 5,576,072 A | 11/1996 | Hostettler et al. | 427/532 |
| 5,662,960 A | 9/1997 | Hostettler et al. | 427/2.3 |
| 5,693,034 A | 12/1997 | Buscemi et al. | 604/265 |
| 5,849,368 A | 12/1998 | Hostettler et al. | 427/536 |
| 5,855,565 A | 1/1999 | Bar-Cohen et al. | 604/104 |
| 5,919,570 A | 7/1999 | Hostettler et al. | 428/424.8 |
| 6,017,577 A | 1/2000 | Hostettler et al. | 427/2.12 |
| 6,030,656 A | 2/2000 | Hostettler et al. | 427/2.3 |
| 6,040,058 A | 3/2000 | Hostettler et al. | 428/457 |
| 6,080,488 A | 6/2000 | Hostettler et al. | 428/423.3 |
| 6,117,296 A | 9/2000 | Thomson | 204/607 |
| 6,120,904 A | 9/2000 | Hostettler et al. | 428/423.3 |
| 6,123,718 A | 9/2000 | Tu et al. | 607/113 |
| 6,249,076 B1 | 6/2001 | Madden et al. | 310/363 |
| 6,265,016 B1 | 7/2001 | Hostettler et al. | 427/2.11 |
| 6,388,043 B1 | 5/2002 | Langer et al. | 528/80 |
| 6,514,237 B1 * | 2/2003 | Maseda | 604/533 |
| 6,679,836 B2 | 1/2004 | Couvillon, Jr. | 600/146 |

(Continued)

FOREIGN PATENT DOCUMENTS

WO 03049658 6/2003

OTHER PUBLICATIONS

U.S. Appl. No. 11/496,248, filed Jul. 31, 2006, Eidenschink et al.

(Continued)

*Primary Examiner* — Theodore J Stigell
(74) *Attorney, Agent, or Firm* — Vidas, Arrett & Steinkraus, P.A.

(57) ABSTRACT

Medical devices or components thereof having electroactive polymer actuators embedded within at least a portion of the device of component thereof, and novel electroactive polymer actuators formed with a conductive substrate layer and an electroactive polymer layer, the electroactive polymer actuated upon application of a voltage to surrounding liquid electrolyte, the actuators may be embedded within an inert polymer matrix material, or within solid polyelectrolyte matrix material.

4 Claims, 9 Drawing Sheets

U.S. PATENT DOCUMENTS

| | | |
|---|---|---|
| 6,749,556 B2 | 6/2004 | Banik .......................... 600/30 |
| 6,770,027 B2 | 8/2004 | Banik et al. .................. 600/146 |
| 6,812,624 B1 | 11/2004 | Pei et al. ..................... 310/800 |
| 6,835,173 B2 | 12/2004 | Couvillon, Jr. .............. 600/146 |
| 6,921,360 B2 | 7/2005 | Banik .......................... 600/30 |
| 6,940,211 B2 | 9/2005 | Pelrine et al. ................ 310/330 |
| 6,960,864 B2 | 11/2005 | Urano et al. ................. 310/307 |
| 6,969,395 B2 | 11/2005 | Eskuri ......................... 606/200 |
| 6,982,514 B1 | 1/2006 | Lu et al. ...................... 310/300 |
| 6,997,870 B2 | 2/2006 | Couvillon, Jr. .............. 600/114 |
| 7,063,671 B2 * | 6/2006 | Couvillon, Jr. .............. 600/562 |
| 7,338,509 B2 * | 3/2008 | Mattison ...................... 606/192 |
| 2002/0037994 A1 | 3/2002 | Yang ........................... 528/422 |
| 2003/0027930 A1 | 2/2003 | Bruckenstein et al. ....... 525/185 |
| 2003/0068522 A1 | 4/2003 | Wang .......................... 428/654 |
| 2003/0236445 A1 | 12/2003 | Couvillon, Jr. .............. 600/114 |
| 2004/0068161 A1 | 4/2004 | Couvillon, Jr. .............. 600/143 |
| 2004/0087982 A1 | 5/2004 | Eskuri ......................... 606/153 |
| 2004/0143160 A1 | 7/2004 | Couvillon, Jr. .............. 600/114 |
| 2004/0172121 A1 | 9/2004 | Eidenschink et al. ....... 623/1.11 |
| 2005/0004425 A1 | 1/2005 | Banik .......................... 600/30 |
| 2005/0085693 A1 | 4/2005 | Belson et al. ................ 600/146 |
| 2005/0102017 A1 | 5/2005 | Mattison ...................... 623/1.11 |
| 2005/0107669 A1 | 5/2005 | Couvillon, Jr. .............. 600/146 |
| 2005/0149161 A1 | 7/2005 | Eidenschink et al. ....... 623/1.11 |
| 2005/0165439 A1 | 7/2005 | Weber et al. ................. 606/191 |
| 2005/0182473 A1 | 8/2005 | Eidenschink et al. ....... 623/1.11 |
| 2005/0183259 A1 | 8/2005 | Eidenschink et al. ........ 29/508 |
| 2006/0041264 A1 | 2/2006 | Eskuri ......................... 606/153 |
| 2006/0111618 A1 | 5/2006 | Couvillon, Jr. .............. 600/152 |
| 2007/0027467 A1 * | 2/2007 | Ortiz et al. ................... 606/198 |
| 2007/0027519 A1 * | 2/2007 | Ortiz et al. ................... 623/1.11 |

OTHER PUBLICATIONS

U.S. Appl. No. 11/272,886, filed Nov. 14, 2005, Mertens et al.
U.S. Appl. No. 11/496,175, filed Jul. 31, 2006, Alkhatib et al.
U.S. Appl. No. 11/496,249, filed Jul. 31, 2006, Jagger et al.
U.S. Appl. No. 11/411,690, filed Apr. 25, 2006, Volk et al.
U.S. Appl. No. 11/368,927, filed Mar. 6, 2006, Volk et al.
U.S. Appl. No. 11/280,120, filed Nov. 16, 2005, Weber et al.
U.S. Appl. No. 11/411,360, filed Apr. 25, 2006, Volk et al.
Santa, Della A. et al., "Steerable Microcatheters Actuated by Embedded Conducting Polymer Structures", *Journal of Intelligent Material Systems and Structures*, vol. 7, May 1996, pp. 292-300.
Madden, John D. et al., "Fast Contracting Polypyrrole Actuators", *Synthetic Metals*, 113 (2000), pp. 185-192.
Maw, S. et al., "Effects of Monomer and Electrolyte Concentrations on Actuation of PPy (DBS) Bilayers", *Synthetic Metals*, 155 (2005), pp. 18-26.
M. Yamaura et al., "Enhancement of Electrical Conductivity of Polypyrrole Film by Stretching: Counter-ion Effect", *Synthetic Metals*, vol. 36, (1988), pp. 209-224.
E. W. H. Jager, E. Smela, O, Inganäs, "Microfabricating Conjugated Polymer Actuators," *Science*, 290, 1540-1545, 2000.
E. Smela, M. Kallenbach, and J. Holdenried, "Electrochemically Driven Polypyrrole Bilayers for Moving and Positioning Bulk Micromachined Silicon Plates," *J. Microelectromechanical Systems*, 8(4), 373-383, 1999.
*Proceedings of the SPIE*, vol. 4329 (2001) entitled Smart Structures and Materials 2001: Electroactive Polymer and Actuator Devices (see, e.g., Madden et al. "Polypyrrole actuators: modeling and performance," pp. 72-83.
Frenot, Audrey et al., "Polymer Nanofibers Assembled by Electrospinning", *Current Opinion in Colloid and Interface Science*, 8 (2003), pp. 64-75.
Mazzoldi A., De Rossi D., "Conductive polymer based structures for a steerable catheter", *SPIE-Int. Soc. Opt. Eng. Proceedings of the SPIE- The International Society for Optical Engineering*, vol. 3987 (2000), pp. 273-280.
Seung-Ki Lee et al., "Biomedical Applications of electroactive polymers and shape-memory alloys", *SPIE-Int. Soc. Opt. Eng. Proceedings of the SPIE- The International Society for Optical Engineering*, vol. 4695 (2002) pp. 17-31.
Guo et al., "Micro Active Guide Wire Catheter System", *Proceedings of the International Conference on Intelligent Robots and Systems*, (1995), pp. 172-177.
Combellas, Catherine, et al., "Surface Modification of Halogenated Polymers 5. Localized Electroless Deposition of Metals on Poly9tetrafluoroethylene) Surfaces," *Journal of Electroanalytical Chemistry556*, (2003) pp. 43-52.
http://www.azom.com... ElectroActive Polymers—EAPs pp. 1-7.
Petrine, Ronald, et al., "Electrostriction of Polymer Dielectrics with Compliant Electrodes as a Means of Actuation," *Sensors and Actuators*, 64 (1998) p. 77-85.
Pelrine, Ron, et al., "High-Speed Electrically Actuated Elastomers with Strain Greater Than 100%," *Science*, vol. 287, (2000), p. 836-839.
D. Zhou et al., "Actuators for the Cochlear Implant," *Synthetic Metals* 135-136 (2003) 39-40.

* cited by examiner

EMBEDDED ELECTROACTIVE POLYMER STRUCTURES FOR USE IN MEDICAL DEVICES

FIELD OF THE INVENTION

The present invention relates to the field of medical devices for implantation or insertion into the body, particularly those having at least a portion of which includes conducting polymer structures.

BACKGROUND OF THE INVENTION

Catheter assemblies, including balloon catheter assemblies which have an expandable balloon member located at the distal end of the balloon catheter, are employed in a variety of medical procedures including as dilatation devices for compressing atherosclerotic plaque which results in a narrowing of the arterial lining, and for delivery and expansion of prosthetic devices such as stents, to a lesion site, i.e. vessel obstruction, within a body vessel.

One medical procedure where balloon catheters are employed is percutaneous transluminal coronary angioplasty (PTCA), or plain old balloon angioplasty (POBA), which is a non-invasive, non-surgical means of treating peripheral and coronary arteries. This technique consists of inserting an uninflated balloon catheter into the affected artery. Dilation of the diseased segment of artery is accomplished by inflating the balloon which pushes the atherosclerotic lesion outward, thereby enlarging the arterial diameter.

In the most widely used form of angioplasty, a balloon catheter is guided through the vascular system until the balloon, which is carried at the distal end of a catheter shaft is positioned across the stenosis or lesion, i.e., vessel obstruction. The balloon is then inflated to apply pressure to the obstruction whereby the vessel is opened for improved flow.

In some embodiments, the catheter balloon may be utilized to expand and/or implant an expandable medical device such as a stent. When the balloon is expanded, the medical device or stent, which is situated on the balloon, is also expanded and released to aid in support and/or repair of the vessel wall.

Due to the very small size of the vessels and the tortuous path through which such devices are inserted and/or implanted, desirable characteristics for such assemblies include flexibility and maneuverability (steerability), for ease of advancement through the body vessel, as well as thin walls, high strength and durability while maintaining a low profile. It is also desirable to control dimensional changes in medical balloons upon inflation to various pressures including both radial and longitudinal expansion characteristics. Thus, the trend has been to downscale device sizes without compromising other device properties.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

The use of conducting polymers as active structures having mechanical characteristics which can be manipulated and which can be transferred to surrounding passive structures can be beneficial for insertable and/or implantable medical devices.

In one aspect, the present invention relates to the use of electroactive polymer (EAP) active regions (actuators) in medical devices which are embedded within a matrix material to improve the flexibility, maneuverability and steerability, durability and strength of a medical device or component thereof.

In one aspect, the present invention relates to embedding EAP within a solid polyelectrolyte matrix which forms a part of the EAP active region.

In another aspect, the present invention relates to embedding EAP active regions within a solid inactive polymer matrix.

As employed herein, the term inactive polymer matrix shall be used to refer to inert or passive polymer materials. Such polymer materials do not actively participate in EAP actuation. For example, polyolefins or other inert polymer materials which have not been modified to provide conductivity, are inactive polymer materials and do not form a part of the EAP active region. Such materials shall be discussed in more detail in the Detailed Description to follow.

Thus, according to the present invention, the matrix material may either form a part of the EAP active region, or not.

The EAP may be embedded within the matrix material in the form of films, fibers, bundles of fibers, particles, etc.

Electroactive polymer active regions may be embedded within an inactive matrix material from which at least a portion of a medical device is formed. In such an embodiment, actuation of the electroactive polymer may depend on fluid ion exchange rather than a solid polyelectrolyte.

In such an embodiment, the inactive polymer matrix may be provided with surface structure such as voids, to allow better access of ions from the surrounding fluid, to the EAP material. Providing such structure can improve the rate of EAP actuation.

The present invention further provides a structure for an active region including EAP, metal and ions derived from a liquid environment. The EAP active region includes a conductive layer and an EAP layer. The ions can be derived from a surrounding fluid including electrolytes. The EAP structure is embedded within a non-active polymer matrix. This structure has been found to provide faster activation as it allows for electrical conductive diffusion over a larger surface area of EAP.

The EAP active regions described herein may be used in any type of medical device, particularly those which are insertable and/or implantable within a body lumen.

The EAP active regions described herein provide, among other things, an improved ability to control the properties of a medical device or aspects of the device.

In various embodiments discussed in the Detailed Description below, the EAP active regions are embedded within the walls of select portions of a catheter assembly including inner and outer shafts, tips, sheaths and expandable balloon members.

These and other aspects, embodiments and advantages of the present invention will become immediately apparent to those of ordinary skill in the art upon review of the Detailed Description and Claims to follow.

BRIEF DESCRIPTION OF THE DRAWINGS

FIG. 3 is a partial longitudinal cross-section illustrating an actuator configuration wherein two EAP active regions, each in bilayer form as illustrated in FIG. 1, are sandwiched together with electrolyte gel disposed between.

DETAILED DESCRIPTIONS OF THE INVENTION

Figure 1:
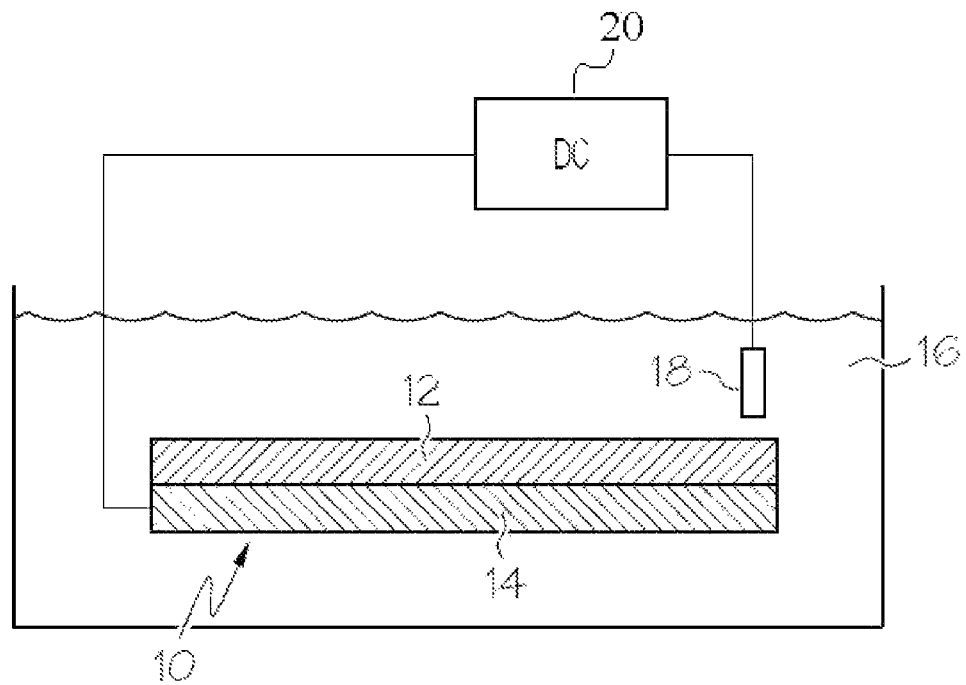
FIG. 1 is a partial longitudinal cross-section of a simplified embodiment of a bilayer EAP active region which may be employed in the present invention.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, or substituted for, elements depicted in another figure as desired.

The present invention relates to the use of electro active polymer (EAP) actuators embedded within a matrix material which forms at least a portion of a medical device or component thereof. The EAP actuators described herein may be used in any type of medical device, particularly those which are insertable and/or implantable within a body lumen. Specific examples of medical devices where the invention described herein may be employed include catheter assemblies and components thereof which are employed for a variety of medical procedures. Examples of catheter assemblies include, but are not limited to, guide catheters, balloon catheters such as PTA and PTCA catheters for angioplasty, catheters for prostate therapy, TTS endoscopic catheters for gastrointestinal use, single operator exchange or rapid exchange (SOE or RX) catheters, over-the-wire (OTW) catheters, fixed wire catheters, medical device delivery catheters including stent delivery devices in both the self-expanding and balloon expandable varieties, catheters for delivery of vena cava filters, catheters for delivery of percutaneous patent foramen ovale (PFO) closure devices, therapeutic substance delivery devices, thrombectomy devices, endoscopic devices, angiographic catheters, neuro catheters, dilitation catheters, urinary tract catheters, gastrointestinal catheter devices, heat transfer catheters including thermal catheters and cooling, intravascular ultrasound systems, electrophysiology devices, and so on and so forth. The above list is intended for illustrative purposes only, and not as a limitation on the scope of the present invention.

Electroactive polymers are characterized by their ability to expand and contract, i.e. volumetric change, in response to electrical stimulation. EAPs can be divided into two categories including electronic EAPs (driven by an electric field) and ionic EAPs (involving mobility or driven by diffusion of ions).

Electronic EAPs (electrorestrictive, electrostatic, piezoelectric, ferroelectric) can be induced to change their dimensions by applied electric fields. Examples of materials in this category include ferroelectric polymers (commonly known polyvinylidene fluoride and nylon 11, for example), dielectric EAPs, electrorestrictive polymers such as the electrorestrictive graft elastomers and electro-viscoelastic elastomers, and liquid crystal elastomer composite materials wherein conductive polymers are distributed within their network structure.

Ionic EAPs are typically employed in connection with the present invention. Ionic EAPs include ionic polymer gels, ionomeric polymer-metal composites, conductive polymers and carbon nanotube composites.

The induced displacement of both electronic EAPs and ionic EAPs can be geometrically designed to bend, stretch, contract or rotate.

Common polymer materials such as polyethylene, polystyrene, polypropylene, etc., can be made conductive through compounding techniques involving the addition of conductive fillers which impart conductive properties to the polymer by forming conductive current-carrying paths within the polymer matrix. The polymer matrix is insulative, but the composite exhibits conductive properties via the filler. These polymers are almost exclusively thermoplastic, but thermosetting materials such as epoxies, may also be employed. Suitable conductive fillers include metals and carbon (usually carbon black or fiber). These can be in the form of sputter coatings or other means can be employed through which a pattern of conductive material can be applied.

Ionic polymer gels are activated by chemical reactions and can become swollen upon a change from an acid to an alkaline environment.

Ionomeric polymer-metal composites can bend as a result of the mobility of cations in the polymer network. Examples of suitable base polymers include, but are not limited to, perfluorosulfonate and perfluorocarboxylate.

Essentially, any electroactive polymer that exhibits contractile or expansile properties may be used in connection with the various active regions of the invention, including any of those listed above.

In some embodiments herein, the ionic EAPs are conductive polymers that feature a conjugated backbone (they include a backbone that has an alternating series of single and double carbon-carbon bonds, and sometimes carbon-nitrogen bonds, i.e. π-conjugation) and have the ability to increase the electrical conductivity under oxidation or reduction. These polymers allow freedom of movement of electrons, therefore allowing the polymers to become conductive. The pi-conjugated polymers are converted into electrically conducting materials by oxidation (p-doping) or reduction (n-doping).

Without being bound to a single theory, conductive polymers (CPs) actuate via the reversible counter-ion insertion and expulsion that occurs during redox cycling. Dimensional or volumetric changes can be effectuated via mass transfer of ions into or out of the polymer. This ion transfer is used to build the conductive polymer actuators. The EAP-containing active region contracts and/or expands in response to the flow of ions out of, or into, the same. For example, in some conductive polymers, expansion is believed to be due to ion insertion between chains, whereas in others inter-chain repulsion is believed to be the dominant effect. Regardless of the mechanism, the mass transfer of ions into and out of the material leads to an expansion or contraction of the polymer, delivering significant stresses (e.g., on the order of 1 MPa) and strains (i.e., up to about 30%). These characteristics are ideal for construction of the devices of the present invention. As used herein, the expansion or the contraction of the active region of the device is generally referred to as "actuation." These exchanges occur with small applied voltages and voltage variation can be used to control actuation speeds.

Upon application of a small voltage, as small as 1 or 2 volts, and proper design of a substrate, ionic EAPs can bend significantly. Ionic EAPs also have a number of additional properties that make them attractive for use in the devices of the present invention, including the following: (a) lightweight, flexible, small and easily manufactured; (b) energy sources are available which are easy to control, and energy can be easily delivered to the EAPS; (c) small changes in potential (e.g., potential changes on the order of 1 volt; d) can be used to effect volume change in the EAPs; (e) relatively fast in actuation (e.g., full expansion/contraction in a few seconds); (f) EAP regions can be created using a variety of techniques, for example, electrodeposition; and (g) EAP regions can be patterned, for example, using photolithography, if desired.

Some commonly known conductive EAPS include, but are not limited to, polypyrroles, polyanilines, polythiophenes, polyethylenedioxythiophenes, poly(p-phenylenes), poly(p-phenylene vinylene)s, polysulfones, polypyridines, polyquinoxalines, polyacetylenes, polyanthraqinones, poly(n-vinylcarbazole)s, etc., with the most common being polythiophenes, polyanilines, and polypyrroles.

Some of the structures are shown below:

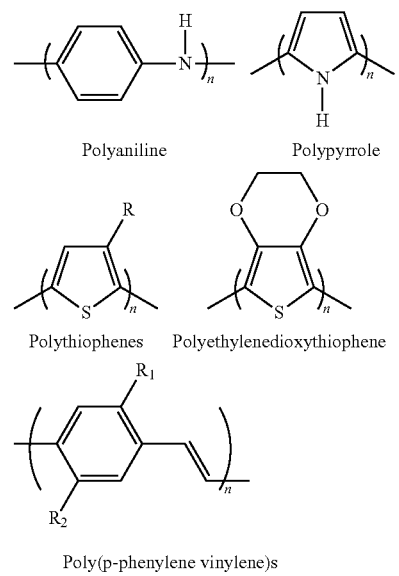

Polyaniline   Polypyrrole

Polythiophenes   Polyethylenedioxythiophene

Poly(p-phenylene vinylene)s

Polypyrrole, shown in more detail below, is one of the most stable of these polymers under physiological conditions:

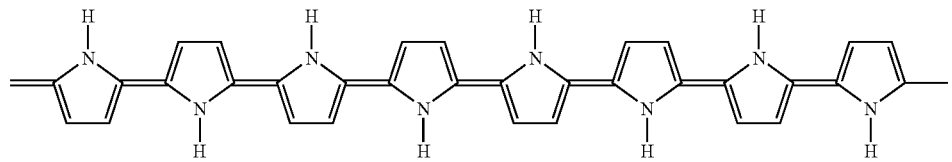

The above list is intended for illustrative purposes only, and not as a limitation on the scope of the present invention.

Networks of conductive polymers may also be employed. For example, it has been known to polymerize pyrrole in electroactive polymer networks such as poly(vinylchloride), poly(vinyl alcohol), NAFION®, a perfluorinated polymer that contains small proportions of sulfonic or carboxylic ionic functional groups, available from E.I. DuPont Co., Inc. of Wilmington, Del.

Electroactive polymers are also discussed in detail in commonly assigned copending U.S. Patent Publication No. 2005/0165439, the entire content of which is incorporated by reference herein.

Additionally, the following components are commonly utilized to bring about electroactive polymer (EAP) actuation: (a) a power source (i.e. a battery), (b) an active region, which comprises the electroactive polymer, (c) a counter electrode and (d) an electrolyte in contact with both the active region and the counter electrode. This will be illustrated in more detail by the following figures.

Furthermore, the behavior of conducting polymers such as the conjugated polymers described herein can be dramatically altered with the addition of charge transfer agents, i.e. ions or dopants. Various dopants can be used in the EAP-containing active regions, such as polypyrrole-containing active regions, including large immobile anions (p-doping) and large immobile cations (n-doping). These materials can be oxidized to a p-type doped material by doping with an anionic dopant species or reducible to a n-type doped material by doping with a cationic dopant species. Generally, polymers such as polypyrrole (PPy) are partially oxidized to produce p-doped materials:

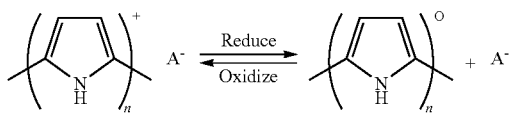

Such oxidation and reduction are believed to lead to a charge imbalance that, in turn, results in a flow of ions into or out of the material. These ions typically enter/exit the material from/into an ionically conductive electrolyte medium associated with the electroactive polymer, typically either a liquid or gel or a solid polyelectrolyte which is coupled to the surface of the electroactive polymer.

Figure 2:
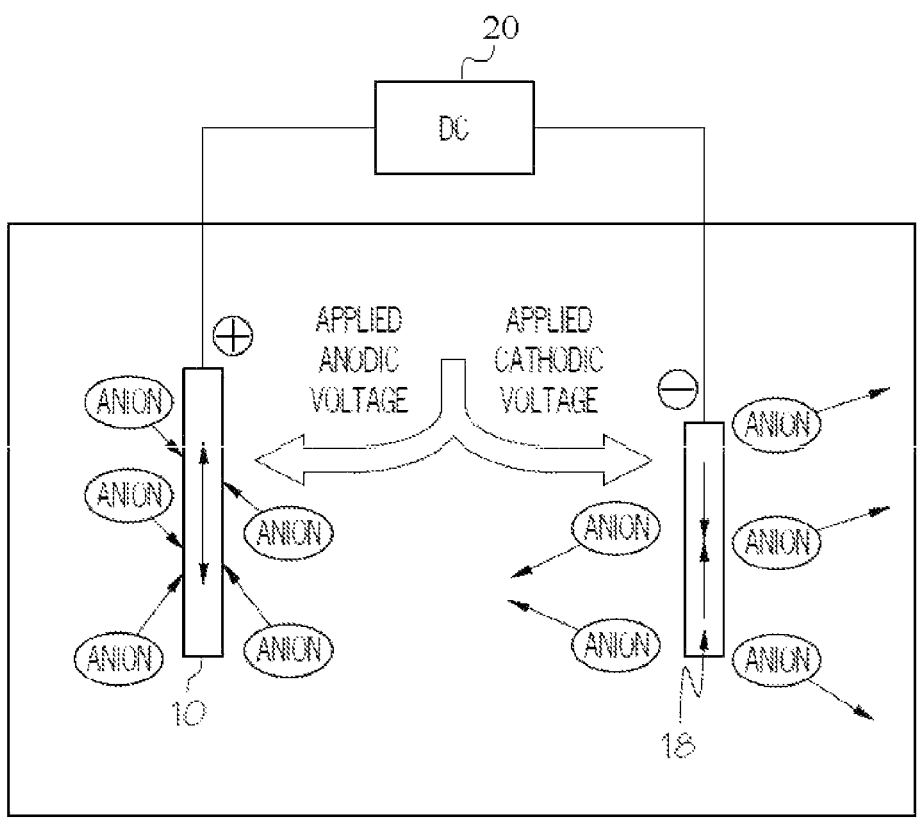
FIG. 2 is a schematic diagram illustrating an embodiment of an electroactive polymer actuator in use.

Expansion or contraction of the active member 12 is a result of these ions moving into (doping) or out of (de-doping) the active member 12 respectively. FIG. 2 is a simple schematic diagram illustrating movement of anions into and out of an active member 12 upon application of an anodic voltage and a cathodic voltage. The active member 12 expands, in this embodiment lengthens, when the anodic voltage is applied causing anions to flow into active member 12. Alternatively, active member 12 contracts, in this embodiment shortens, when cathodic voltage is applied causing anions to flow out of active member 12. The movements of anions into the active member 12 may be referred to in the art as doping, and the movement of anions out of the active member 12, may be referred to as de-doping. These ions, or dopants, enter the polymer from the ionically conductive electrolyte medium. If the electroactive polymer has already been doped, and ions are already present in the polymer, they may exit the polymer.

As mentioned above, various dopants can be used herein including large immobile anions and large immobile cations. According to one specific embodiment, the active region comprises polypyrrole (PPy) doped with dodecylbenzene sulfonate (DBS) anions. When placed in contact with an electrolyte containing small mobile cations, for example, Na$^+$ cations, and when a current is passed between the polypyrrole-containing active region and a counter electrode, the cations are inserted/removed upon reduction/oxidation of the polymer, leading to expansion/contraction of the same. This process can be represented by the following equation:

$$PPy^+(DBS^-)+Na^++e^- \rightleftharpoons PPy^\circ(Na^+DBS^-)$$

where Na$^+$ represents a sodium ion, e$^-$ represents an electron, PPy$^+$ represents the oxidized state of the polypyrrole, PPy$^\circ$ represents the reduced state of the polymer, and species are enclosed in parentheses to indicate that they are incorporated into the polymer. In this case the sodium ions are supplied by the electrolyte that is in contact with the electroactive polymer member. Specifically, when the EAP is oxidized, the positive charges on the backbone are at least partially compensated by the DBS$^-$ anions present within the polymer. Upon reduction of the polymer, however, the immobile DBS$^-$ ions cannot exit the polymer to maintain charge neutrality, so the smaller, more mobile, Na$^+$ ions enter the polymer, expanding the volume of the same. Upon re-oxidation, the Na$^+$ ions again exit the polymer into the electrolyte, reducing the volume of the polymer.

Referring now to the figures, FIG. 1 is a schematic cross-sectional view of one embodiment of a bilayer EAP active region 10 according to the invention including each of the elements used in the disclosed EAP active region 10. This is a simplified schematic view of an EAP active region 10 which may be then embedded within a polymer matrix for use in medical devices according to the invention. This is discussed in more detail below.

While the embodiment shown in FIG. 1 is directed to a bilayer EAP actuator, such is not intended to limit the scope of the present invention. Other configurations of EAP actuators may also be employed. Bilayer EAP actuators are discussed in Santa, Della A. et al., "Steerable Microcatheters Actuated by Embedded Conducting Polymer Structures", *Journal of Intelligent Material Systems and Structures*, vol. 7, May, 1996, pages 292-299 and in Madden, John D. et al., "Fast contracting polypyrrole actuators", *Synthetic Metals*, 113 (2000), pp. 185-192, and in Maw, S. et al., "Effects of monomer and electrolyte concentrations on actuation of PPy (DBS) bilayers", *Synthetic Metals* 155 (2005), pp. 18-26, each of which is incorporated by reference herein.

Active member 12 shown in FIG. 1, may be formed from any electroactive polymer material such as the conjugated polymers or other conductive polymers discussed above, as well as mixtures of such polymers. In this embodiment, active member 12 is shown coupled to a conductive substrate layer 14 suitably in the form of a metal film or other conductive backing. In this embodiment, active region 10 is shown immersed in an electrolyte solution for purposes of discussing the features of an EAP actuator only. It should be noted that typically, it is not desirable for the conductive substrate layer 14 to be in direct contact with an electrolyte 14 because it may corrode or react in the presence of an electrolyte.

Any number of procedures may be employed to provide active member 12 with a conductive substrate layer 14 including, but not limited to, sputtering, gilding, casting, etc. the polymer onto a metal substrate, electrochemically depositing the polymer onto the metal, thermal evaporation, vapor deposition, etc. For further discussion of this technique, see U.S. Pat. No. 6,982,514, the entire content of which is incorporated by reference herein.

Conductive substrate layer 14 may act as the working electrode. Conductive substrate layer 14 is in electrical connection with a voltage supply 20. A counter electrode, submersed other otherwise in contact with electrolyte 16, is also shown in contact with a voltage supply 20, and completes the electrical circuit. See FIGS. 4a and 4b, for example, of U.S. Pat. No. 6,982,514 incorporated by reference herein.

In the embodiment shown in FIG. 1, active member 12 includes an electro active polymer that contracts or expands in response to the flow of ions out of, or into, the active member 12. If active member 12 is placed in contact with an electrolyte 16, free ions provided by the electrolyte 16, may diffuse into or out of active member 12. Ions flowing into the active polymer member 12 result in expansion and ions flowing out of the active polymer member 12 result in contraction. In this embodiment, electrolyte 16 is provided by an electrolytic solution which comes into contact with active member 12 in order to allow for the flow of ions between electrolyte solution 16 and active member 12.

Electrolyte 16 may come into contact with only a portion of the surface of active member 12, or up to the entirety of the surface of active member as is shown in FIG. 1. However, it is most desirable that conductive substrate 14, is not placed in direct contact with electrolyte 16.

In this embodiment, active member 12 is shown in film form. However, active member 12 may be employed in other forms such as fibers or groups of fibers or a combination of multiple films and fibers and fibers may be bundled as well.

Active member 12 includes an electroactive polymer. Many electroactive polymers having desirable tensile properties are known to persons of ordinary skill in the art. Examples of common suitable electroactive polymers include, but are not limited to, polypyrroles, polyanilines, polythiophenes, polyethylenedioxythiophenes, poly(p-phenylenes), poly(p-phenylene vinylene)s, polysulfones, polypyridines, polyquinoxalines, polyacetylenes, polyanthraqinones, poly(n-vinylcarbazole)s, etc.

In a specific embodiment, active member 12 is a polypyrrole film. Such a polypyrrole film may be synthesized by electrodeposition according to the method described by M. Yamaura et al., "Enhancement of Electrical Conductivity of Polypyrrole Film by Stretching: Counter-ion Effect," *Synthetic Metals*, vol. 36, pp. 209-224 (1988), which is incorporated herein by reference. In addition to polypyrrole, any conducting polymer that exhibits contractile or expansile properties may be used within the scope of the invention. Polyaniline is an example of such a usable conducting polymer.

Conductive substrate layer 14 may be formed from any suitable conductive material such as another conducting polymer or a metal such as gold (Au) or platinum (Pt), or a metal alloy, for example.

In one embodiment, the active member 12 is an ion-exchange polymer and the conductive substrate layer 14 is a noble metal referred to as an ion-exchange polymer-noble metal composite. In a specific embodiment, the active member is polypyrrole or polyaniline and the noble metal is gold or platinum. These ion-exchange polymer-noble metal composites are advantageous for use herein because thin strips can be employed to obtain large bending and displacement with low voltage compared to many other actuators, such as piezoceramics or shape metal alloys.

Electrolyte 16 may be, for example, a liquid, a gel, or a solid, so long as ion movement is allowed. One example of a liquid electrolyte is a saline-based contrast solution.

Counter electrode 18 is in electrical contact with electrolyte 16 in order to provide a return path for charge to a source 20 of potential difference between conductive substrate layer 14 and electrolyte 16. Counter electrode 18 may be any electrical conductor, for example, another conducting polymer or a metal such as gold or platinum, etc. In order to actuate active region 10, a current is passed between active conductive substrate layer 14 and counter electrode 18 inducing movement of ions which in turn induces contraction or expansion of member 12 depending on the flow of ions out of or into the EAP.

FIG. 1 illustrates only one example of actuator configuration, in this embodiment, a bilayer actuator. The actuators can be provided in an essentially infinite array of configurations as desired, including planar actuator configurations (e.g., with planar active members and counter-electrodes), cylindrical actuator configurations (e.g., see the actuator illustrated in FIG. 1), and so forth. Some configurations are disclosed in U.S. Pat. No. 6,249,076, the entire content of which is incorporated by reference herein. Other configurations are disclosed in U.S. Pat. No. 6,679,836. A specific example of an alternative configuration of an EAP actuator is one wherein an electroactive polymer layer is coupled to a solid polyelectrolyte or a gel polyelectrolyte which is in contact with an electrode or conductive substrate as shown in FIG. 1. This type of actuator is illustrated in FIG. 1 of copending U.S. patent application Ser. No. 11/496,248, the entire content of which is incorporated by reference herein.

Figure 3:
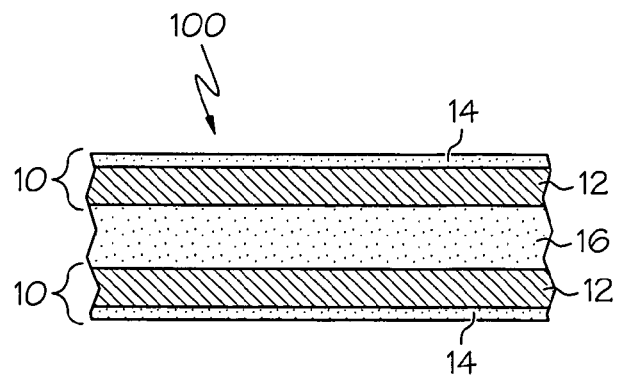

In another specific embodiment, two bilayer EAP active regions 10 formed using a conductive substrate layer or electrode 14 and an active polymer layer 12, similar to that shown in FIG. 1, are sandwiched together and an electrolyte 16, such as a gel electrolyte is disposed between the two active regions 10 to form an EAP active region 100 as shown as a partial cross-section in FIG. 3. Electrode 14 of each active region 10 can be connected to a voltage source and a counter electrode 14, also connected to a voltage source, can be used to create a potential difference such that electrolytes flow into and out of active polymer layer 12 causing expansion/contraction of active polymer layer 12. This is only an example of an alternative configuration of an EAP actuator and is not intended as a limitation on the scope of the present application.

Additional information regarding EAP actuators, their design considerations, and the materials and components that may be employed therein, can be found, for example, in E. W. H. Jager, E. Smela, O. Inganäs, "Microfabricating Conjugated Polymer Actuators," *Science*, 290, 1540-1545, 2000; E. Smela, M. Kallenbach, and J. Holdenried, "Electrochemically Driven Polypyrrole Bilayers for Moving and Positioning Bulk Micromachined Silicon Plates," *J. Microelectromechanical Systems*, 8(4), 373-383, 1999; and *Proceedings of the SPIE*, Vol. 4329 (2001) entitled "Smart Structures and Materials 2001: Electroactive Polymer and Actuator Devices (see, e.g., Madden et al, "Polypyrrole actuators: modeling and performance," at pp. 72-83), each of which is hereby incorporated by reference in its entirety.

The EAP actuators according to the invention may be embedded within an inactive or active polymer matrix material which forms at least a portion of a medical device or component thereof, specific examples of which are found below.

In the case where the polymer matrix material forms a part of the EAP actuator itself, the polymer matrix material may be selected from solid polyelectrolytes such as solid elastomeric polyelectrolytes.

Solid polyelectrolytes (SPE) are those polymers whose conductivity is due to ionic species. Such materials are complexes of high molecular weight polymers and metal salts or liquid solutions of metal salts trapped in a polymer matrix. One polymer which can be employed is polyacrylonitrile which has been prepared by dissolving the polymer in ethylenecarbonate/propylenecarbonate/sodiumperchlorate solution. See *Steerable Microcatheters actuated by Embedded Conducting Polymer Structures*, A. Della Santa et al., Journal of Intelligent Material Systems and Structures, Vol. 7, pages 292-300 (May 1996), the content of which is incorporated by reference herein.

Alternatively, inactive polymer matrix materials may be employed. Examples of suitable inactive polymer materials which can be employed as a polymer matrix material include, but are not limited to, polymer suitable in the formation of medical devices may be employed herein, examples include, but are not limited to, homopolymers, copolymers and terpolymers of olefins including homopolymers, copolymers and terpolymers of ethylene, butylene and propylene; rubbery block copolymers such styrenic block copolymers; polyamides; polyurethanes including polyether, polyester and polyurea type polyurethanes; polyethers; polyesters and copolyesters; poly(amide-block-ether) block copolymers; poly(ether-ester) copolymers; poly(ester-ester) copolymers; poly(ester-amide) copolymers; poly(amide-ether) copolymers; polycarbonates; polyimides; polyketones; polysulfones; polycyclooctane; etc. Suitable copolymers and terpolymers not specifically discussed herein can be formed of many monomers and are known to those of skill in the art.

Examples of olefin homopolymers include polyethylene and polypropylene. Suitable olefin copolymers include, but are not limited to, ethylene vinyl actetate copolymers, ethylene n-butyl acrylate copolymers, ethylene (meth)acrylate copolymers, ethylene ethylacrylate copolymers, etc.

Examples of suitable rubbery block copolymers include A-B-A triblock structures, A-B diblock structures, $(A-B)_n$ radial block copolymer structures, as well as branched and grafted versions of such, wherein the A endblock is a non-elastomeric polymer block, typically comprising polystyrene, and the B block is an unsaturated conjugated diene or hydrogenated version thereof. In general, the B block is typically isoprene, butadiene, ethylene/butylene (hydrogenated butadiene), ethylene/propylene (hydrogenated isoprene), and mixtures thereof. Examples of block copolymers having an unsaturated conjugated diene include, but are not limited to, styrene-isoprene-styrene (SIS) and styrene-butadiene-styrene (SBS). Other useful block copolymers include styrene-ethylene/butylenes-styrene (SEBS) and styrene-ethylene/propylene-styrene (SEPS). Commercial embodiments include the Kraton.® G and D series block copolymers, available from Kraton Polymer Company Houston, Tex.), Europrene® Sol T block copolymers available from EniChem (Houston, Tex.), Vector® block copolymers available from Exxon (Dexco) (Houston, Tex.), Solprene® block copolymers from Housmex® (Houston, Tex.), etc.

Block copolymers include poly(ether-block-amide)s available from Atofina under the tradename of PEBAX® find utility herein.

Examples of suitable polyester elastomers include poly (ester-block ether) elastomers such as those sold under the tradename of HYTREL® available from DuPont de Nemours & Co., and those sold under the tradename of ARNITEL® available from DSM Engineering Plastics; etc.

Suitable polyesters include polyalkylene naphthalates such as polyethylene terephthalate and polybutylene terephthalate.

Examples of suitable polyamides include, but are not limited to, PA12, PA6 and PA66, also be referred to in the art as nylon 12, nylon 6 and nylon 66.

Shape memory polymers may also be employed.

In this embodiment, wherein the matrix is formed from an inactive polymer, upon insertion of the medical device into the body, the surrounding fluid can act as the electrolyte, thereby providing a source of ions for actuation once a counterelectrode is in place which is in contact with a source of electrical potential. Thus, ions can be induced to flow into or out of the EAP layer depending on whether the current supplied is anodic or cathodic as shown in FIG. 2 discussed above. A saline contrast solution could be employed as an electrolyte solution as well.

Figure 4:
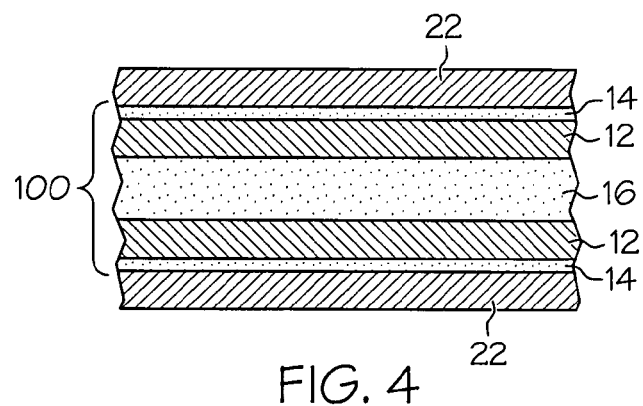
FIG. 4 is a partial longitudinal cross-section of an actuator configuration similar to that shown in FIG. 3 embedded within polymer matrix material.

FIG. 4 is a partial longitudinal cross-section of an EAP active region 100 of the type shown in FIG. 3 embedded within an inactive polymer matrix 22 such as polyethylene, for example.

Figure 5:
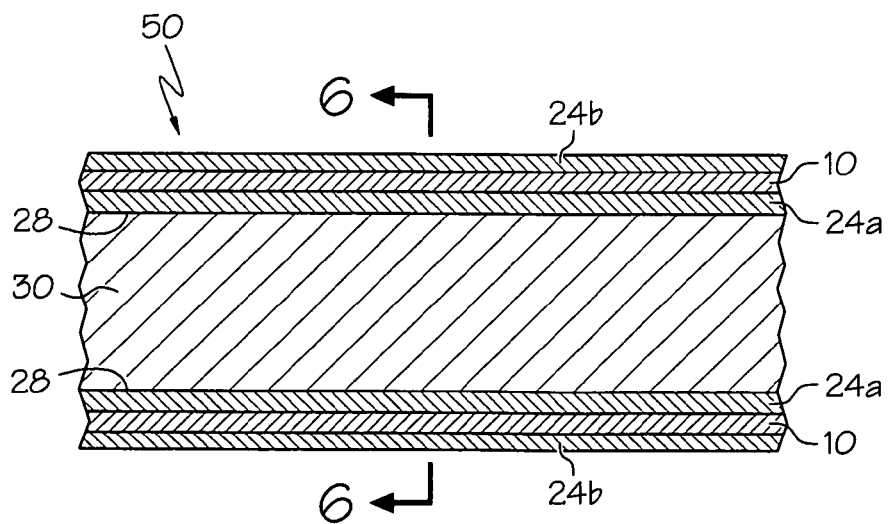
FIG. 5 is a partial longitudinal cross-sectional view of a tubular assembly with an EAP active region embedded with two tubular substrates.

FIG. 5 is partial longitudinal cross-section of an alternative embodiment wherein an EAP active region 10 of a bilayer configuration similar to that shown in FIG. 1 is embedded within the wall of tubular substrates 24a, 24b, which are both formed from an inactive polymer matrix material forming a tubular assembly 50. Tubular substrates 24a, 24b may be formed from the same polymer material, or may each be formed from a different polymer material.

Figure 6:
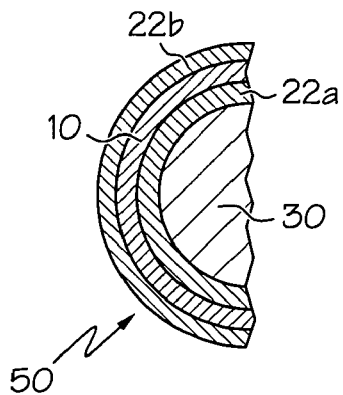
FIG. 6 is a radial cross-section taken at section 6-6 in FIG. 5.

FIG. 6 is a radial cross-section taken at 6-6 in FIG. 5.

These tubular assemblies may be formed using any method known in the art. As an illustration, a tubular substrate 24a formed from a material which has a low coefficient of friction, sometimes referred to in the art as a lubricious surface, such as a fluoropolymer, e.g. polytetrafluoroethylene (PTFE) may be coated with a layer of gold using any suitable technique known in the art. Examples of suitable methods include, but are not limited to, sputter coating, electroless deposition, vapor deposition, electroplating, etc. over the PTFE tube to form the conductive layer 14 of the EAP actuator. Pretreatment of the PTFE may be required for some of the procedures as is known in the art.

In another specific example, a coated polyimide such as KAPTON® HN-100 available from DuPont de Nemours & Co. in Wilmington, Del. may be coated with a conductive metal layer followed by PPy as described in "Effects of monomer and electrolyte concentrations on actuation of PPy (DBS) bilayers" at page 19.

Figure 7:
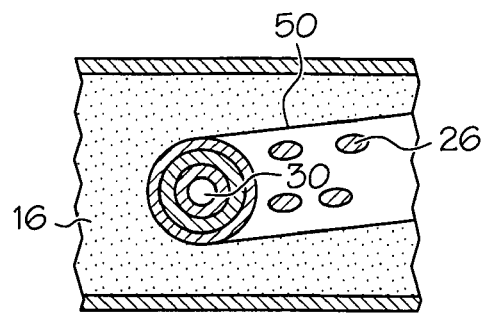
FIG. 7 is a tubular assembly with a configuration similar to that shown in FIG. 5 in an electrolyte solution wherein outer tubular substrate of tubular assembly has voids therein.

An active polymer layer 12, formed from polypyrrole (PPy) may be deposited on the gold layer using any suitable techniques as discussed above, for example, by electropolymerization. In the case where outer substrate 24b has voids, as shown in FIG. 7, the outer tubular member can be formed using any method known in the art such as through extrusion techniques. As an alternative to the embodiment shown in FIG. 7, the inner surface of the outer tubular substrate 24b, can be configured with impressions which form reservoirs for retaining liquid or gel electrolyte. A radial cross-section of a tubular substrate with the inner surface 25 of outer tubular substrate 24b configured with reservoirs 27 shown retaining an electrolyte 16 which is in contact with EAP active region 10. Active region 10 is shown configured as in FIG. 9 such that the active polymer layer 12 is in contact with electrolyte 16 held in reservoirs. The inner surface 25 of outer tubular substrate 24b may be metallized with an appropriately conductive material such as gold or platinum as described above.

Figure 9:
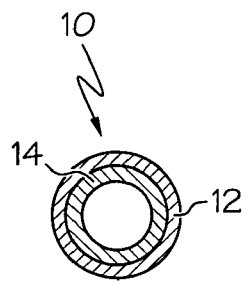
FIG. 9 is an enlarged radial cross-section of EAP active region 10 which may be employed in the embodiment shown in FIG. 8.
Figure 10:
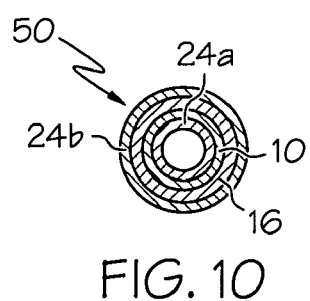
FIG. 10 is a radial cross-section of an alternative tubular assembly having an EAP active region embedded therein.

Referring to FIG. 10, in an alternative embodiment, a layer of electrolyte 16, such as a gel electrolyte, may be deposited and then a tubular structure 24b of a heat shrinkable material may be disposed about whole assembly and appropriately treated with heat to cause shrinkage thereby entrapping the gel layer. Such heat shrinkable tubes are known in the art and may be formed from any suitable material such as a polyolefin or copolymer thereof. FIG. 9 again is illustrative of the configuration of active region 10 showing active polymer layer 12 and conductive layer 14. A suitably conductive wire such as gold or platinum, can be wrapped about the assembly prior to shrinking the heat shrinkable outer tubular substrate 24b over the assembly for purposes of a counter electrode. Furthermore, conductive substrate layer 14, which can function as the working electrode, is also contact with a voltage source, and has been discussed above. Providing that a potential difference is created to allow ions to flow between the electrolyte 16 and the active polymer layer 12, any suitable electrode/counter electrode configuration may be employed. It may be desirable that the wire run the entire length of the assembly such that dissipation of energy is minimized along the tubular assembly.

The electrolyte alternatively, may be capture in an interpenetrating polymer network (IPN), or in a fibrous network in order to improve retention of the gel electrolyte layer 16 on the active polymer layer 12.

Methods of capturing gels in interpenetrating polymer networks (IPNs) are disclosed in commonly assigned U.S. Pat. Nos. 5,693,034, 6,265,016, 6,120,904, 6,080,488, 6,040,058, 6,030,656, 6,017,577, 5,919,570, 5,849,368, 5,662,960, 5,576,072, each of which is incorporated by reference herein in their entirety.

Fibers may be applied to the active polymer layer 12 using any suitable technique known in the art. A specific method of applying fibers is electrospinning. See Frenot, Audrey et al., "Polymer nanofibers assembled by electrospinning", *Current Opinion in Colloid and Interface Science*, 8 (2003), pp. 64-75, which is incorporated by reference herein.

In each case, the resultant assembly may be dipped in electrolyte, a gold wire wound around the tube and then a shrink wrap tube as described above may be heat shrunk around the whole assembly.

For some embodiments, a liquid electrolyte may be employed rather than a gel. For example, in the case of a fibrous network wherein a dipping method of applying electrolyte is employed, a liquid electrolyte may also be used.

Electrolyte may be made available to the active polymer layer 12 of the EAP actuator 10 in a variety of other ways as well such as by forming voids 26 within the substrate layer 24b as shown in partial perspective view in FIG. 7. The configuration of EAP active region 10 employed may be substantially the same as that shown in FIG. 1, such that when the entire assembly is exposed to an electrolyte solution, for example, ions from the electrolyte solution are free to flow to active polymer layer 12 upon actuation. Of course, actuation requires a potential differential to be created by an electrode/counter electrode as described above.

Alternatively, the electrolyte may be placed in lumen 30 of tubular substrate (not shown) defined by the inner surface 25 of tubular substrate 24a such as in the form of a gel electrolyte, for example. In this embodiment, desirably voids are created in tubular substrate 24a, and the active region 10 would take on an opposite configuration as shown in FIG. 1 such that active polymer layer 12 is exposed to the gel electrolyte. Alternatively, in the case of an expandable balloon member, for example, the inflation media employed to expand the balloon member may contain electrolyte.

Figure 8:
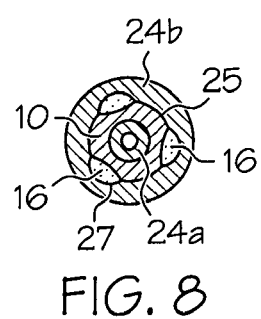
FIG. 8 is a radial cross-section of another embodiment of a tubular assembly having an EAP active region embedded therein.

In yet another alternative embodiment, while the construction is substantially the same as that shown in FIG. 5, the tubular substrates 32a, 32b are formed using a solid polyelectrolyte and actually participate in actuation of the active polymer layer 12 which is part of the active region 10 shown in FIG. 1 forming tubular assembly 60. FIG. 8 is a partial longitudinal cross-sectional representation of this embodiment and FIG. 9 is a radial cross-section taken at 9-9 in FIG. 8. Alternatively, one of the tubular substrates 32a, 32b, may be formed from an inactive polymer matrix material as long as the solid polyelectrolyte forms the member which is in contact with the active polymer layer 12 as shown in FIG. 1.

Providing that the EAP actuator includes the basic elements for functioning, i.e., the conductive layer, the active polymer layer, electrolyte, and suitable electrode/counter electrode combination, a variety of configurations may be employed herein.

The EAP actuators described herein can be employed in any of a variety of medical devices. For example, the EAP actuators as described herein, may be employed in at least a portion of catheter assemblies and components thereof including, but not limited to, tips, inner shaft, outer shaft, retractable sheaths, expandable balloon members, etc.

In some embodiments, the electroactive polymer is embedded within the at least a portion of the polymer matrix from which the inner shaft, outer shaft or sheath of a catheter assembly is formed.

In one specific embodiment, the electroactive polymer is embedded within at least a portion of the distal end of an outer catheter shaft, the shaft being formed from either non-active polymer or from solid polyelectrolyte. When the EAP is actuated, the diameter of the outer catheter shaft may expand, thereby anchoring the shaft to a vessel wall to maintain position of the catheter device while a medical device such as a stent is deployed.

The outer catheter shaft may also have two or more sections of which include EAP in a matrix. The first diameter of the outer shaft is smaller than the second diameter so that when actuated, the two EAP sections block off a section of the body lumen thereby allowing more accurate targeted release of a therapeutic agent to a targeted area.

A plurality of expandable sections of EAP within the catheter shaft may also be employed for increasing the size of a body lumen.

The electroactive polymer system may be embedded in a helical pattern within the matrix material of the distal inner catheter shaft on which a balloon is mounted to provide the inner catheter shaft with a twisting function to improve folding/rewrapping of a catheter balloon. An example of such a twisting mechanism which could utilize EAP is described in U.S. patent application Ser. No. 11/272,886, filed Nov. 14, 2005, the entire contents of which being incorporated herein by reference.

Other examples of such applications are disclosed in commonly assigned copending U.S. patent application Ser. No. 11/496,175.

In at least one embodiment, retractable sheaths are formed from a matrix material wherein at least a portion thereof has electroactive polymer embedded therein. When the EAP is actuated, the sheath radially expands, thereby increasing the diameter and lessening the friction between the distal sheath and the loaded stent in order to reduce deployment forces when the sheath is retracted from over the stent. Again, the EAP actuator may be embedded within the sheath in a variety of configurations including in tubular form, or helically, for example.

In another embodiment, the EAP actuator is embedded within the proximal end of a distal sheath to allow for longitudinal lengthening (actuation)/shortening (deactuation) of the distal sheath.

In some embodiments existing catheter configurations may be modified by including EAP in the form of a matrix as described herein. Some examples of such configurations are described in commonly assigned copending U.S. Patent Publication No. 2008/0027528, and U.S. Patent Publication No. 2007/0249909, each of which is incorporated by reference herein in its entirety.

In another aspect, the present invention relates to expandable medical balloons formed from a matrix material, and embedded within at least a portion of the matrix material, is an electroactive polymer actuator. The EAP actuators may be embedded within the body, waist and/or cone portions and any combination thereof.

Figure 11:
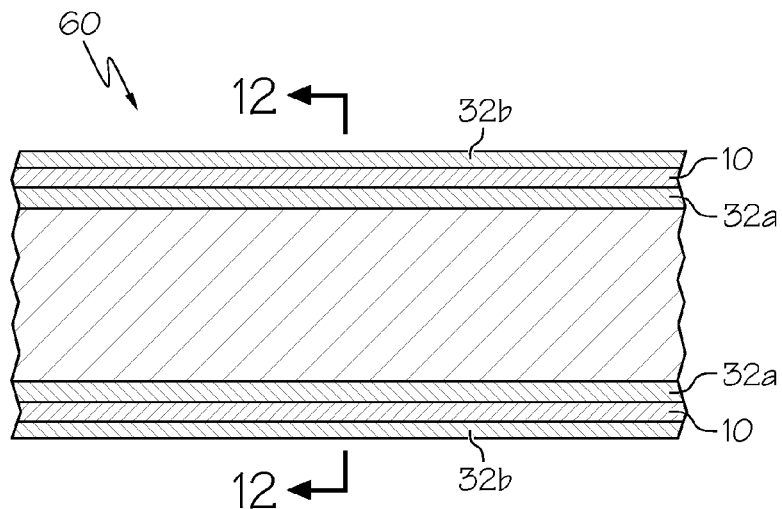
FIG. 11 is a partial longitudinal cross-section of a tubular assembly according to the invention having EAP active region embedded therein.
Figure 12:
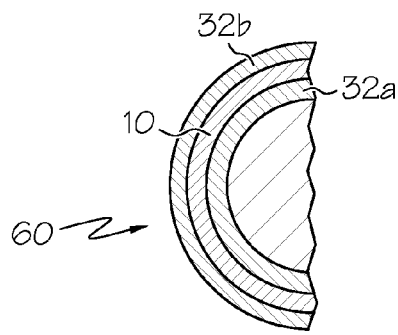
FIG. 12 is a radial cross-section taken at 12-12 in FIG. 11.
Figure 12A:
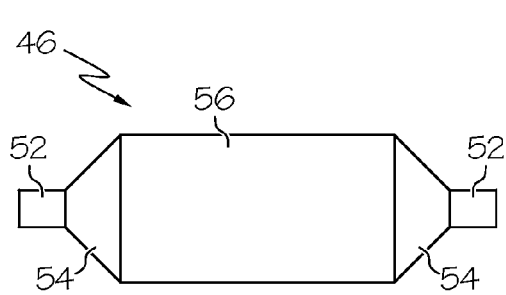
FIG. 12A is a side view of a balloon wherein EAP active regions as shown in FIGS. 11 and 12 may be embedded therein.

FIG. 12A is a side view illustrating an expandable balloon member 46 having waist portions 52, cone portions 54 and a body portion 56. As discussed above, EAP active regions as shown in FIGS. 11 and 12 may be embedded in waist portions 52, cone portions 54, body portion 56, or any combination thereof.

The electroactive polymer system may be embedded within the matrix material so as to facilitate folding and rewrapping, and to provide improved expansion and/or contraction control. In some embodiments, the EAP is embedded within the body portion, cone portions and/or waist portions to facilitate balloon folding and rewrap. For example, strips of EAP actuator embedded within the balloon wall and uniformly spaced radially about the balloon circumference can assist in balloon collapse upon deactuation of the EAP strips.

The following examples of methods of embedding the actuator within the polymer matrix material from which the balloon is formed, are intended for illustrative purposes only, and not as a limitation on the scope of the present invention.

The balloon can be formed using any suitable method known in the art. In general, the steps may include 1) extruding a balloon perform; and 2) radially expanding the balloon preform into a balloon mold. Of course, other steps may be included in the process as well. A description of a method of balloon formation can be found in U.S. Pat. No. 4,490,421, the entire content of which is incorporated by reference herein.

Once the balloon has been formed a conductive layer can be applied to the balloon or a portion thereof using any suitable method as described above such as by sputter coating a layer, i.e. gold, platinum, or the like, for example, onto the balloon. An active polymer layer can then be deposited onto the conductive layer using any suitable method as described above such as by electrodeposition, for example. For embedding the layer, another polymer layer may then be applied over the active polymer layer so as to surround the active polymer layer using any suitable technique.

Alternatively, prior to radial expansion of the balloon preform into a balloon mold, a thin layer of conductive material can be applied as described above, followed by the addition of the active polymer layer such as by photopolymerization (i.e. soft lithography). Once a very thin layer of EAP actuator has been applied, the preform can then be placed into the balloon mold and radially expanded.

Alternatively, a second pre-blown balloon can be assembled over the first so as to encompass the actuator between the two, and then do a final radial expansion into a second balloon mold followed by a heat set.

Other methods for achieving EAP active regions on only portions of the balloon, may include entirely coating the balloon or balloon preform, and then selectively removing material via known techniques such as by chemical or laser ablation, or by subtractive machining, for example.

Alternatively, preformed strips of EAP actuator which already includes an active polymer layer and a conductive layer, can be adhered to the balloon preform such as by adhesive bonding or by laser heat bonding such as with a $CO_2$ laser, for example, the preform placed into the balloon mold, and then radially expanded therein. This then can be followed by other polymer layers.

Alternatively, a second tube of polymer can be placed concentrically over a first coextruded tube, the actuator including at least one conductive layer and at least one active polymer layer therebetween, and the tubular assembly then placed into a balloon mold and radially expanded therein. The first and second coextruded tube can be made from the same or different polymer matrix materials. For example, the inner tube may be PTFE, and the outer tube a polyolefin or copolymer thereof, a block copolymer such as poly(ether-block-amide) block copolymer, or a polyester such as polyalkylene terephthalate (i.e. PET or PBT) or a copolyester.

These preformed strips of EAP actuator can also be embedded within the balloon wall using coextrusion techniques as is known in the art.

As discussed above, the polymer matrix material can be inactive polymer matrix material or active polymer matrix material, i.e. solid polyelectrolyte. If inactive, exposure of the active polymer layer of the actuator to electrolyte may be accomplished using methods as disclosed above.

Strips of EAP actuator embedded within polymer layers which form the balloon wall, can be advantageously positioned on the balloon so as to aid in balloon folding.

In some embodiments, the balloon can be formed with two, three, four, five, six or more wings. For example, for a three wing balloon structure, by positioning three longitudinal EAP active regions uniformly about the balloon circumference, these EAP active regions can aid in balloon folding upon contraction/deactuation of the EAP active region.

Figure 12B:
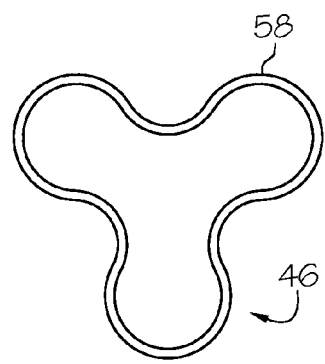
FIG. 12B is a radial cross-section illustrating a folded balloon having a three-wing configuration.

FIG. 12B is a radial cross-section of a balloon of the type shown in FIG. 12A in a deflated state and having three wings 58. As discussed above, balloon 46 may have two, three, four, five, six or more wings as well. EAP actuators as shown in FIGS. 11 and 12, may be embedded within the wings 58 to facilitate folding.

Thus, in these embodiments, the balloon wings can include EAP actuators embedded therein in order to facilitate balloon folding and rewrap. These types of applications are disclosed in commonly assigned copending U.S. patent application Ser. No. 11/496,248, the entire content of which is incorporated by reference herein.

In another embodiment, a catheter assembly is provided with a sheath of polymer matrix material having EAP embedded in at least a portion of the sheath. The sheath is provided over a catheter balloon for retaining the balloon in a folded configuration during delivery through a body lumen to the lesion site. This protective sheath may cover all or only a portion or portions of the expandable balloon.

The EAP actuators according to the invention may be embedded within a catheter tip for controlling the profile of the tip during withdrawal, for example, or to provide the tip with a bending function. Applications of this type are disclosed in commonly assigned copending U.S. patent application Ser. No. 11/368,927, the entire content of which is incorporated by reference herein.

The EAP actuators disclosed herein also find utility in catheters and components thereof which are employed within a bifurcated vessel. For example, the EAP actuators may be employed in combination with catheter delivery systems employed for delivery of medical devices, such as stents or stent-grafts, to the site of a bifurcated vessel, such as inner and/or outer shafts and balloons. For example, EAP embedded within the distal end region of a bifurcation catheter can be employed wherein when activated, it rotates the catheter into alignment with the side branch bifurcation.

Another embodiment of the present invention is directed to EAP embedded within the side branch guide wire lumen which when activated expands, rotates, and twists the side branch into alignment. Some examples of assemblies where a side branch guidewire housing could be modified to incorporate a matrix of EAP material to provide the desired alignment characteristics are shown and described in Published U.S. Patent Application Numbers: 2005-0149161-A1; 2004-0172121-A1; 2005-0182473 A1 the entire content of each being incorporated herein by reference.

Another embodiment of the present invention with respect to a bifurcation vessel is directed to EAP embedded within the wall of a balloon which when activated allows for fine rotation of the balloon into proper alignment with the side branch. See U.S. patent application Ser. No. 11/591,848 for a discussion of applications involving bifurcated vessels, the entire content of which is incorporated by reference herein.

Figure 13:
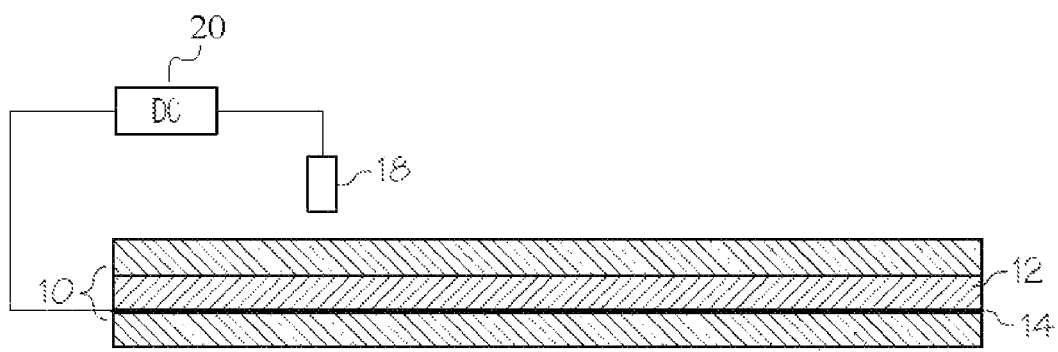
FIG. 13 is a schematic illustrating initial configuration of an EAP active region embedded within a polymer matrix prior to activation.
Figure 14:
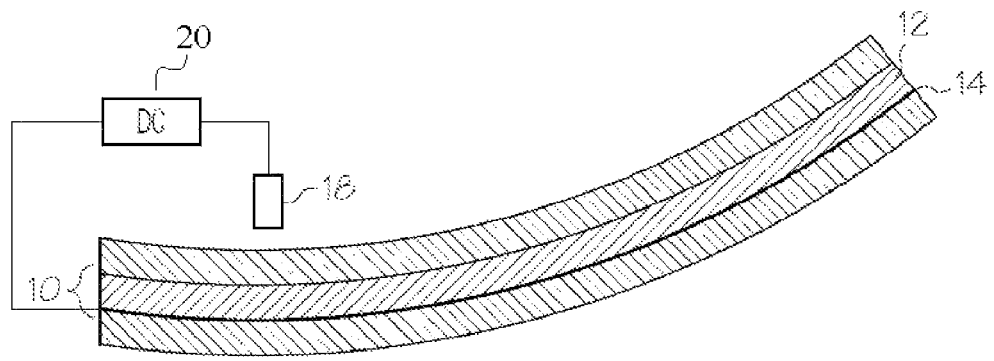
FIG. 14 is a schematic illustrating EAP deformation as a result of an applied electrical potential.

In other embodiments, the EAP can be induced to bend upon actuation. Bending, rather than stretching/contracting or expanding/contracting, can be accomplished by design. For example, one method is to employ a polymer matrix material which is flexible, but elongates less than the specific EAP selected. FIG. 13 is a schematic illustrating and bilayer EAP active region 10, formed of an active polymer layer 12 and a conductive substrate layer 14 which is in communication with a power source 20. Furthermore, a counter electrode 18 is shown in connection with the power source. A source of electrolytes (not shown) must be in communication with the active polymer layer 12. Any of the numerous methods as described above, may be employed. The actuated bended configuration can be reversed upon reversal of the applied external voltage.

In one embodiment, this bending phenomenon can be employed for creating a catheter assembly which exhibits improved crossing of a lesion. In some instances, there is difficulty in getting the catheter assembly to cross the lesion because it is difficult to center the catheter at the lesion within a tortuous vessel.

Figure 15:
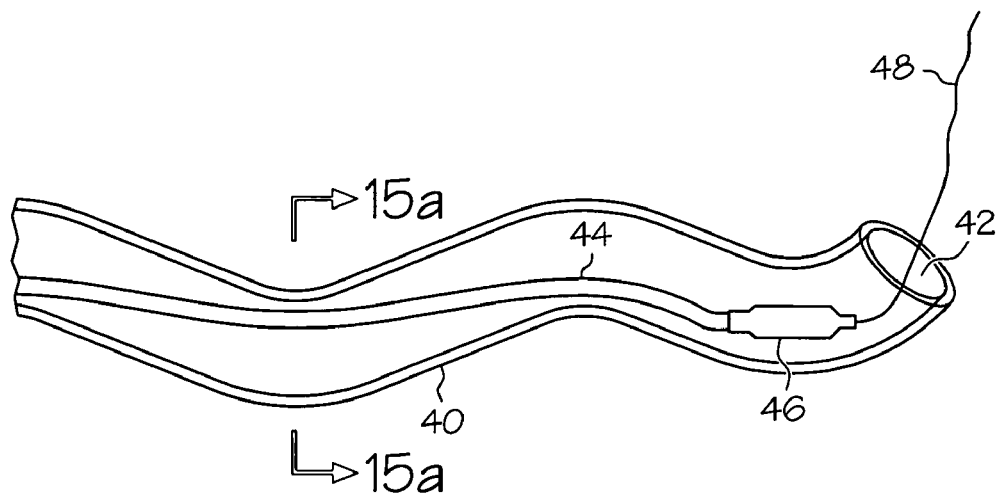
FIG. 15 is a side perspective view of a catheter in an environment of use.
Figure 15A:
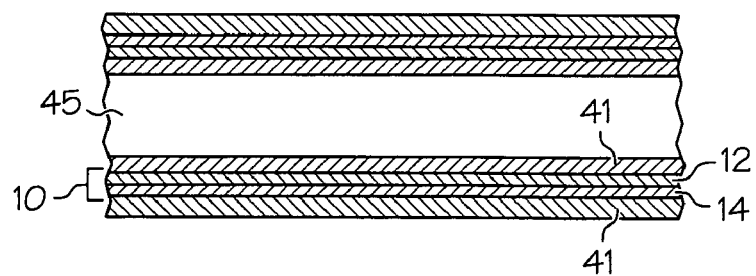
FIG. 15a is a longitudinal cross-section of a catheter taken at 15a-15a in FIG. 15.

FIG. 15 is a side perspective view of a catheter assembly in an environment of use, i.e. a blood vessel, for example. In this embodiment, vessel 40 is shown with a chronic total occlusion (CTO) 42. A catheter having a shaft 44 with an expandable balloon member 46 disposed at the distal end of catheter shaft 44 is shown within the vessel. A guide wire 48 shown pushed through the CTO 42. FIG. 15A is an exploded cross-section taken at section 15a-15a in FIG. 15. A lumen 45 is shown. This may be a guide wire lumen, or it may be a lumen through which a second catheter shaft (not shown) may be disposed. As is known in the art, catheter assemblies may include both an inner and an outer shaft, either or both of which may incorporate EAP actuator in at least a portion of the wall therein. The entire distal portion of the catheter shaft may have EAP active region 10 embedded therein, or sections of the catheter shaft may have EAP active region 10 embedded therein. EAP active region 10 is shown as a bilayer configuration having an active polymer layer 12 and a conductive layer 14. Of course, for actuation, conductive layer 10 is in contact with a power source (not shown) and a counter electrode (also not shown) is necessary to create the required potential difference as discussed above.

Prior to actuation of EAP, it is difficult to align the catheter within the CTO 42.

Figure 16:
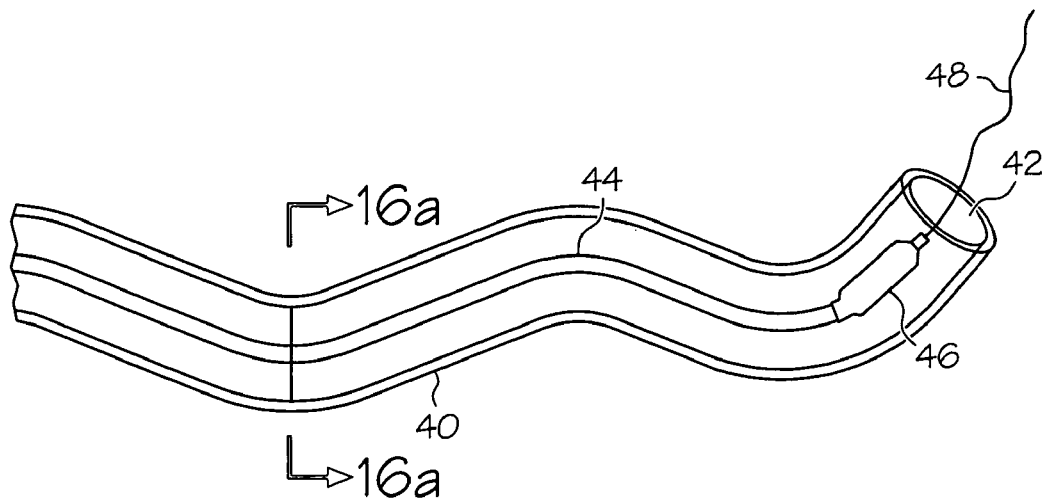
FIG. 16 is a side perspective view of a catheter similar to that shown in FIG. 15 in an environment of use after actuation of EAP active region.
Figure 16A:
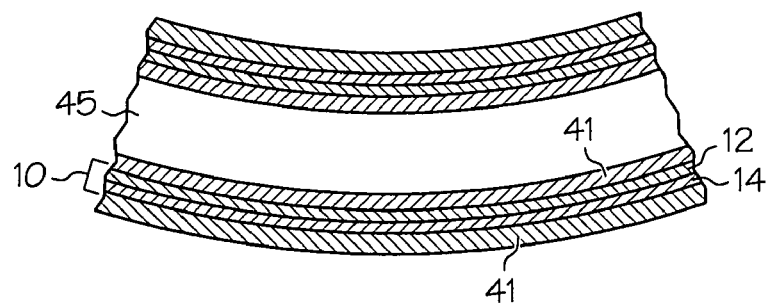
FIG. 16a is a longitudinal cross-section taken at 16a-16a in FIG. 16.

FIG. 16 is a side perspective view of a catheter assembly similar to that shown in FIG. 15 after EAP active region 10 has been actuated. FIG. 16a is taken at section 16a-16a of catheter shaft 44 in FIG. 16 in order to show EAP active region 10 embedded within the catheter wall 41.

Figure 17:
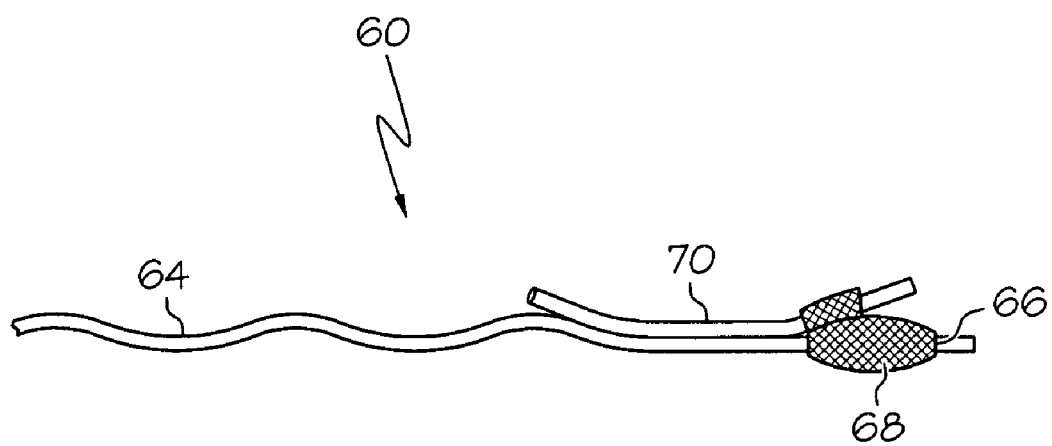
FIG. 17 is a side view of a simplified bifurcated catheter assembly employing EAP in the catheter shaft.
Figure 18:
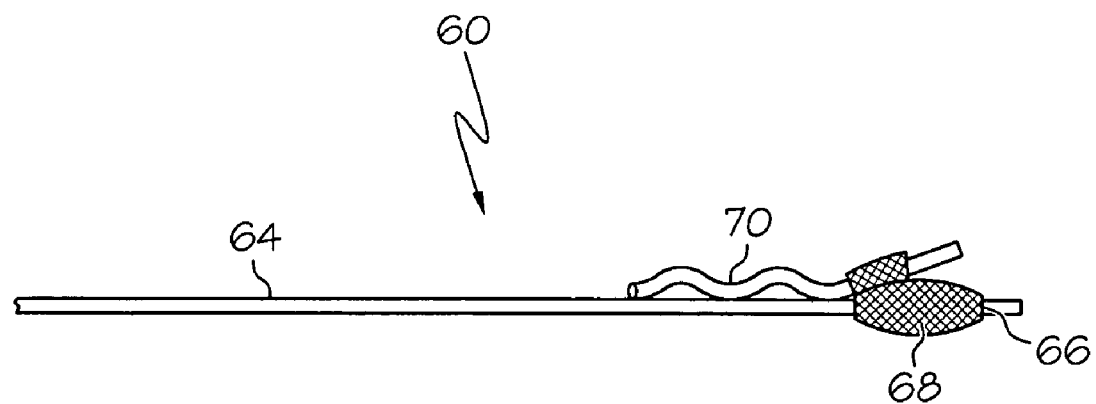
FIG. 18 is a side view of a bifurcated catheter assembly employing EAP in the side branch housing.

In another embodiment, EAP active region is employed in a bifurcated catheter assembly. Bifurcated catheter assembly 60 is shown in FIG. 17 as a perspective side view and includes a shaft 64 having an expandable balloon member 66 disposed about the distal end and a stent 68 for a bifurcated vessel shown disposed over the expandable balloon member 66. Catheter 60 is further shown with a side branch housing 70 for a second guide wire. This is a simplified catheter assembly employed for illustrative purposes only. For purposes of having increased control over positioning of the catheter assembly 60, either the shaft 64 (FIG. 17) may have EAP active region embedded in at least a portion thereof, or, the side branch housing 70 (FIG. 18) may have EAP active region embedded therein. Please refer to FIGS. 15a and 16a.

Figure 19:
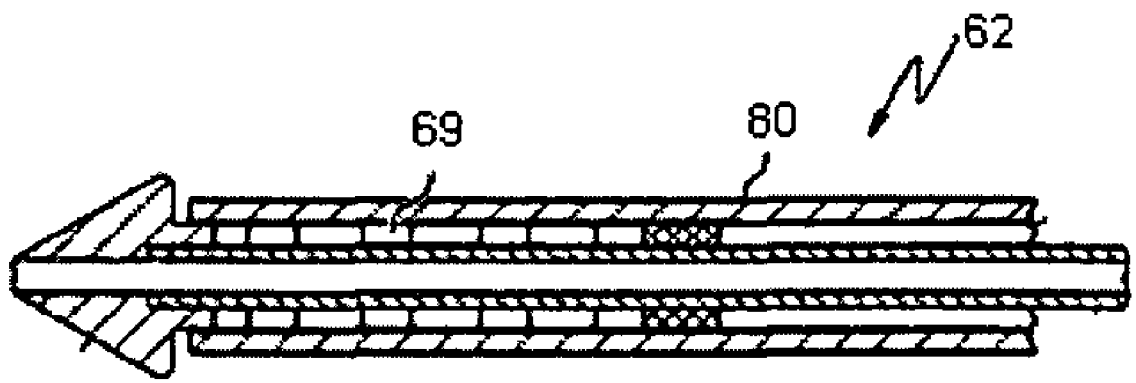
FIG. 19 is a side view of a catheter with a sheath disposed about the length of the stent.

FIG. 19 is a side view of a catheter assembly 62 illustrating a sheath 80 disposed about a stent 69. Sheath 80 is formed in accordance with the inventive tubular structures as shown in FIGS. 1-14.

Again, catheter assemblies, as is known in the art, commonly employ inner and outer shafts which are not shown above. Either the inner and/or outer shaft may incorporate EAP active regions in a portion or in all of the walls of the inner and/or outer shaft.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A catheter assembly, the catheter assembly comprising a retractable sheath and a stent, the sheath having a longitudinal axis and formed from a matrix material, and embedded within at least a portion of the matrix material helically about the longitudinal axis, is an electroactive polymer actuator, wherein the matrix material is a solid polyelectrolyte or a non-active polymer material, the sheath is disposed about the stent and whereupon actuation of the electroactive polymer actuator, the sheath radially expands from a first diameter to a second diameter.

2. The retractable sheath of claim 1 wherein said electroactive polymer actuator comprises an electroactive polymer layer and a conductive substrate layer.

3. The retractable sheath of claim 1 wherein said electroactive polymer actuator comprises an electroactive polymer layer, a conductive substrate layer and at least one solid, polyelectrolyte layer or gel polyelectrolyte layer.

4. The retractable sheath of claim 1 wherein said matrix material comprises a solid polyelectrolyte.

* * * * *